(12) United States Patent
Fan et al.

(10) Patent No.: US 8,071,781 B2
(45) Date of Patent: Dec. 6, 2011

(54) PROCESS FOR PREPARING RABEPRAZOLE SODIUM

(75) Inventors: Chin-Tsai Fan, Sinying (TW);
Chen-Ming Hsiao, Sinying (TW);
Rong-Bin Hsieh, Sinying (TW)

(73) Assignee: Syn-Tech Chem. & Pharm. Co., Ltd., Sinying (TW)

( * ) Notice: Subject to any disclaimer, the term of this patent is extended or adjusted under 35 U.S.C. 154(b) by 413 days.

(21) Appl. No.: 12/268,580

(22) Filed: Nov. 11, 2008

(65) Prior Publication Data

US 2010/0121068 A1    May 13, 2010

(51) Int. Cl.
*C07D 401/12* (2006.01)

(52) U.S. Cl. .................................... 546/273.7

(58) Field of Classification Search ............... 546/273.7
See application file for complete search history.

(56) References Cited

U.S. PATENT DOCUMENTS

| | | | |
|---|---|---|---|
| 6,180,652 B1 | 1/2001 | Tsujii et al. | |
| 6,545,024 B1 | 4/2003 | Tsujii et al. | |
| 6,919,459 B2 | 7/2005 | Broeckx et al. | |
| 2005/0288334 A1 | 12/2005 | Kohl et al. | |
| 2006/0014798 A1 | 1/2006 | Turchetta et al. | |
| 2007/0225500 A1 | 9/2007 | Kohl et al. | |
| 2008/0090877 A1 | 4/2008 | Yoko et al. | |

FOREIGN PATENT DOCUMENTS

| | | |
|---|---|---|
| WO | WO03008406 A1 | 1/2003 |
| WO | WO03082858 A1 | 10/2003 |
| WO | WO2004052882 A1 | 6/2004 |
| WO | WO2006013960 A1 | 2/2006 |
| WO | WO2007023393 A2 | 3/2007 |
| WO | WO2007091276 A2 | 8/2007 |
| WO | WO2008017020 A2 | 2/2008 |

*Primary Examiner* — Patricia Morris
(74) *Attorney, Agent, or Firm* — Ming Chow; Sinorica, LLC

(57) ABSTRACT

The present invention provides a process for preparing the amorphous rabeprazole sodium. The process comprises the following steps: (a) Contacting rabeprazole sodium compound with a solvent system to thereby obtain a clear solution under a first temperature, wherein said solvent system is a mixture of at least two categories of organic solvents; (b) Stirring said clear solution of step (a) under a second temperature for a certain time period to obtain a solution containing resultant separated solid, wherein said second temperature is equal to or lower than said first temperature; (c) Filtering said solution containing resultant separated solid obtained from step (b) to obtain a wet solid; and (d) Drying said wet solid to obtain an amorphous rabeprazole sodium compound.

11 Claims, 1 Drawing Sheet

PROCESS FOR PREPARING RABEPRAZOLE SODIUM

BACKGROUND OF THE INVENTION

1. Technical Field

The present invention relates to a process of preparation of a chemical compound; and more particularly, to a process of preparation and purification of a proton pump inhibitor.

2. Description of Related Art

Rabeprazole, as represent by Formula I, is one of the proton pump inhibitors of the benzimidazole-type, and is also the common name for 2-({[4-(3-Methoxypropoxy)-3-methylpyridin-2-yl]methyl}sulfinyl)-1H-benzimidazole. The sodium salt of rabeprazole (i.e., rabeprazole sodium) is an inhibitor for the gastric proton pump, which can suppress the secretion of gastric acid via inhibiting the $H^+$, $K^+$ ATPase at the gastric secretory surface of partial cells without effect on cholinergic or histamine $H_2$-receptors. Rabeprazole sodium is usually used in the prescription of the combinatory therapies for the eradication of *Helicobacter pylori*.

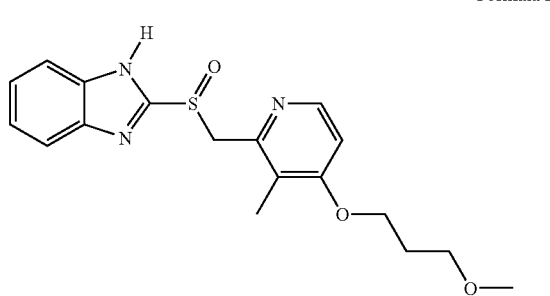

Formula I

The conventional method for producing rabeprazole is as illustrated in the U.S. Pat. No. 5,045,552. After oxidation with m-chloroperbenzoic acid in dichloromethane at −45° C., quenched with triethylamine, followed by drying over magnesium sulfate, then 2-({[4-(3-Methoxypropoxy)-3-methylpyridin-2-yl]methyl}sulfinyl)-1H-benzimidazole, namely the rabeprazole acid, is obtained. This crude product is processed by adding to an aqueous sodium hydroxide solution and then distilling twice together with ethanol for the removal of $H_2O$, and finally drying in vacuum. To this end, the final product of rabeprazole sodium is amorphous. Another conventional method disclosed in US2004/0180935A1 to obtain amorphous rabeprazole sodium is to dissolve rabeprazole acid in a mixture of sodium hydroxide in methanol at 25° C.-35° C. and the product is precipitated by adding petroleum ether. The precipitated solid is then filtered, washed and then dried at 50° C.-60° C. for 12 hours.

In order to purify the rabeprazole sodium from the impurities produced in the synthetic process, several methods are used, such as that U.S. Pat. No. 6,180,652 discloses a process for forming the acetone complex of the rabeprazole sodium. This acetone complex, however, is not suitable for the manufacture of medicinal compounds.

There is a need to provide an alternative process for purifying the amorphous rabeprazole sodium, especially in a more convenient and more efficient way than the conventional methods.

SUMMARY OF THE INVENTION

The present invention provides a process for preparing the amorphous rabeprazole sodium. The process comprises the following steps: (a) contacting rabeprazole sodium compound with a solvent system to thereby obtain a clear solution under a first temperature, wherein said solvent system is a mixture of at least two categories of organic solvents; (b) stirring said clear solution of step (a) under a second temperature for a certain time period to obtain a solution containing resultant separated solid, wherein said second temperature is equal to or lower than said first temperature; (c) filtering said solution containing resultant separated solid obtained from step (b) to obtain a wet solid; and (d) drying said wet solid to obtain an amorphous rabeprazole sodium compound.

The present invention also provides a pharmaceutical composition comprising a rabeprazole sodium obtained from the process according to the present invention and a pharmaceutically acceptable carrier, excipient or diluent.

Therefore, one of the objects of the present invention is to provide a process for preparing amorphous rabeprazole sodium without forming acetone complex in the process.

Another object of the present invention is to provide a process for preparing amorphous rabeprazole sodium more efficiently and more conveniently.

Yet another object of the present invention is to provide a pharmaceutical composition comprising a rabeprazole sodium obtained from the process according to the present invention and a pharmaceutically acceptable carrier, excipient or diluent, wherein no acetone complex is formed in the process.

And, still another object of the present invention is to provide a pharmaceutical composition comprising a rabeprazole sodium more efficiently and more conveniently obtained from the process according to the present invention and a pharmaceutically acceptable carrier, excipient or diluent.

BRIEF DESCRIPTION OF THE DRAWINGS

The invention as well as a preferred mode of use, further objectives and advantages thereof, will best be understood by reference to the following detailed description of an illustrative embodiment when read in conjunction with the accompanying drawings, wherein.

DETAILED DESCRIPTION OF THE PREFERRED EMBODIMENT

Figure 1:
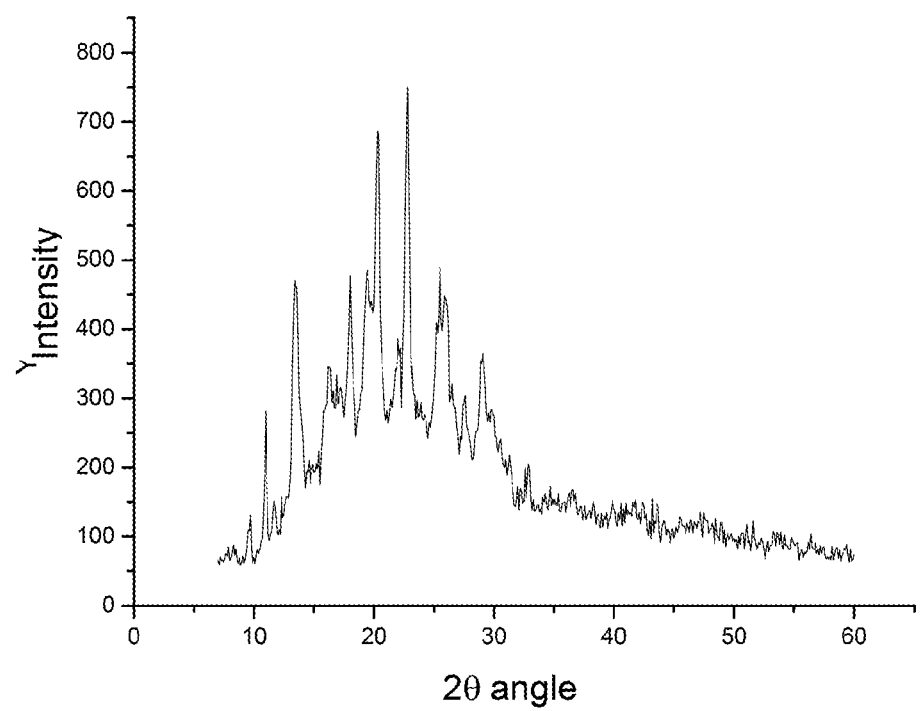
FIG. 1 is an X-ray diffraction pattern of the rabeprazole sodium purified by the process according to the present invention.

While the present invention discloses a process of preparing rabeprazole sodium, it is to be stated first of all that the detailed organic chemical synthesis of rabeprazole or the processing procedures relay on known technology and need not be discussed at length herein.

In one preferred embodiment of the present invention, it discloses a process for preparing rabeprazole sodium. The process comprising the following steps:

(a) Contacting rabeprazole sodium compound with a solvent system to thereby obtain a clear solution under a first temperature, wherein said solvent system is a mixture of at least two categories of organic solvents.

(b) Stirring said clear solution of step (a) under a second temperature for a certain time period to obtain a solution containing resultant separated solid, wherein said second temperature is equal to or lower than said first temperature.

(c) Filtering said solution containing resultant separated solid obtained from step (b) to obtain a wet solid.

(d) Drying said wet solid to obtain an amorphous rabeprazole sodium compound.

Firstly, according to step (a), the rabeprazole sodium compound obtained from the corresponding synthesis process, such as an extract crude obtained from condensing a solution comprising rabeprazole compound and sodium hydroxide, is dissolved in a solvent system comprising at least two categories of organic solvents. The resultant solution is clear. That is, the rabeprazole sodium compound was almost completely dissolved in the solvent system. This step is carried out under a first temperature that ranges from room temperature to a moderately high temperature, preferably from about 25° C. to about 50° C.

Suitable solvent system for conducting step (a), but not limited are a ketone solvent mixing with a cyclic hydrocarbon solvent, a ketone solvent mixing with an ether solvent, or a heterocyclic organic solvent mixing with a cyclic hydrocarbon solvent.

In this embodiment, when the solvent system is the mixture of a ketone solvent and a cyclic solvent, the suitable ketone solvent includes, but is not limited to methylethylketone, acetone, and mixtures thereof. In the meantime, the suitable cyclic hydrocarbon solvent includes, but is not limited to cyclohexane, cycloheptane, benzene, toluene, or xylene. Besides, the suitable vol/vol ratio of the cyclic hydrocarbon solvent to the ketone solvent is preferable from about 0.3 to about 5, whereas said ratio is about 0.5 when the cyclic hydrocarbon solvent used is cyclohexane and said ratio is about 3 when the cyclic hydrocarbon solvent used is toluene.

Furthermore, when the solvent system is a mixture of methylethylketone, acetone and cyclic hydrocarbon solvent, the preferable relative volumetric ratio of each solvent is described below:

(1) The volume of acetone is one;
(2) The methylethylketone solvent has a volume of about 6 to 10 times to the volume of acetone and is preferable about 10 times; and
(3) The cyclic hydrocarbon solvent has a volume of about 20 to 30 times to the volume of acetone and is preferable 30 times.

When the solvent system is the mixture of a ketone solvent and an ether solvent, the suitable ether solvent includes, but is not limited to diethyl ether, isopropylethyl ether, or diisopropyl ether and the suitable ketone solvent is as previously described. Besides, the suitable vol/vol ratio of the ketone solvent to the ether solvent is preferable from about 1.5 to about 5.

When the solvent system is the mixture of a heterocyclic organic solvent and a cyclic hydrocarbon solvent, the suitable heterocyclic organic solvent includes, but is not limited to tetrahydrofuran and the suitable cyclic hydrocarbon solvent is as previously described. Besides, the suitable vol/vol ratio of the cyclic hydrocarbon solvent to the heterocyclic organic solvent is preferable from about 0.2 to about 5, whereas said ratio is about 5 when the cyclic hydrocarbon is toluene, is about 0.6 when the cyclic hydrocarbon solvent is cyclohexane, and is about 2.4 when the cyclic hydrocarbon solvent is xylene.

After conducting step (a) and the rabeprazole sodium is almost completely dissolved in said solvent system, the resultant clear solution is then stirred under a second temperature for a certain time period to obtain a solution containing resultant separated solid, wherein said second temperature is equal to or lower than said first temperature described in step (a). The resultant solid is rabeprazole sodium with higher purity. The time period of stirring is preferable more than about 3 hours and much preferable more than 12 hours. Optionally, if the temperature of the solution obtained from step (a) is elevated above the room temperature, during stirring the resultant clear solution is preferably cooled gradually to the room temperature or even to at least about 10° C. This cooling step is preferable because it helps accelerate the resultant solid to separate from the solution.

After conducting step (b) and the rabeprazole sodium with higher purity is separate from the solution, the solution containing resultant separated solid is then filtered to obtain a wet solid of rabeprazole sodium with higher purity. Optionally, the wet solid of rabeprazole sodium with higher purity is preferable washed by the same solvent system used in step (a) to remove the residue of sodium hydroxide and other impurities.

Finally, the wet solid of rabeprazole sodium obtained in step (c) is then dried, and an amorphous rabeprazole sodium compound is obtained. The drying process can be carried out by means of evaporation, vacuum suction, or lyophilization. The yield of the amorphous rabeprazole sodium is more than about 80% and its purity is more than 99% by HPLC.

FIG. 1 represents the X-ray diffraction pattern of the final product purified by the solvent system comprising methylethylketone and toluene. Besides, the X-ray diffraction pattern of this rabeprazole is quite distinctive from what disclosed in the U.S. Pat. No. 6,545,024. As shown in FIG. 1, the X-ray diffraction pattern of the rabeprazole sodium comprising some crystalline features and is characterized in that the 2-theta diffraction angles and the corresponding intensities are (9.3, 131), (11.7, 151), (13.6, 462), (18.0, 478), (19.5, 485), (20.3, 688), (22.8, 752), (25.2, 411), (25.5, 490), (27.6, 305), and (29.1, 366), (32.9, 205).

Several specific examples of this invention are described in details and as below, and are provided only for purpose of illustration and are not intended to limit the scope of the invention as disclosed in the claims.

Example 1

Preparation of Amorphous Rabeprazole Sodium by the Solvent System Comprising Methylethylketone and Cyclohexane 10.0 grams of rabeprazole sodium compound is dissolved in 50 ml of methylethylketone and heated to 40° C., followed by adding 25 ml of cyclohexane. The solution is clear, and the insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of methylethylketone and cyclohexane. After dried, the X-ray diffraction pattern of this final product does not have any distinct diffraction peaks so that the final product of this process is amorphous. The final product of amorphous rabeprazole sodium obtained is 8.8 grams, so the yield of this process is 88%. The purity of this amorphous rabeprazole sodium obtained is 99.3% by HPLC.

Example 2

Preparation of Amorphous Rabeprazole Sodium by the Solvent System Comprising Methylethylketone and Cyclohexane 10.0 grams of rabeprazole sodium compound is dissolved in a solution prepared by mixing 50 ml of methylethylketone and 25 ml of cyclohexane. The solution is heated to 45° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of methylethylketone and cyclohexane. After dried, the X-ray diffraction pattern of this final product does not have any distinct diffraction peaks so that the final product of this process is amorphous. The final product of amorphous rabeprazole sodium obtained is 8.9 grams, so the yield of this process is 89%. The purity of this amorphous rabeprazole sodium obtained is 99.3% by HPLC.

Example 3

Preparation of Amorphous Rabeprazole Sodium by the Solvent System Comprising Methylethylketone and Toluene 10.0 grams of rabeprazole sodium compound is dissolved in a solution prepared by mixing 50 ml of methylethylketone and 150 ml of toluene. The solution is heated to 45° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of methylethylketone and toluene. After dried, the X-ray diffraction pattern of this final product does not have any distinct diffraction peaks so that the final product of this process is amorphous. The final product of amorphous rabeprazole sodium obtained is 8.5 grams, so the yield of this process is 85%. The purity of this amorphous rabeprazole sodium obtained is 99.5% by HPLC. The X-ray diffraction pattern of the final product is shown in FIG. 1.

Example 4

Preparation of Amorphous Rabeprazole Sodium by the Solvent System Comprising Tetrahydrofuran and Toluene 10.0 grams of rabeprazole sodium compound is dissolved in a solution prepared by mixing 50 ml of tetrahydrofuran and 150 ml of toluene. The solution is heated to 45° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of tetrahydrofuran and toluene. After dried, the X-ray diffraction pattern of this final product does not have any distinct diffraction peaks so that the final product of this process is amorphous. The final product of amorphous rabeprazole sodium obtained is 8.3 grams, so the yield of this process is 83%. The purity of this amorphous rabeprazole sodium obtained is 99.4% by HPLC.

Example 5

Preparation of Amorphous Rabeprazole Sodium by the Solvent System Comprising Tetrahydrofuran and Cyclohexane 10.0 grams of rabeprazole sodium compound is dissolved in a solution prepared by mixing 50 ml of tetrahydrofuran and 30 ml of cyclohexane. The solution is heated to 45° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of tetrahydrofuran and cyclohexane. After dried, the X-ray diffraction pattern of this final product does not have any distinct diffraction peaks so that the final product of this process is amorphous. The final product of amorphous rabeprazole sodium obtained is 8.2 grams, so the yield of this process is 82%. The purity of this amorphous rabeprazole sodium obtained is 99.2% by HPLC.

Example 6

Preparation of Amorphous Rabeprazole Sodium by the Solvent System Comprising Tetrahydrofuran and Xylene 10.0 grams of rabeprazole sodium compound is dissolved in a solution prepared by mixing 50 ml of tetrahydrofuran and 120 ml of xylene. The solution is heated to 45° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the same solvent mixture of tetrahydrofuran and xylene. After dried, the X-ray diffraction pattern of this final product does not have any distinct diffraction peaks so that the final product of this process is amorphous. The final product of amorphous rabeprazole sodium obtained is 8.3 grams, so the yield of this process is 83%. The purity of this amorphous rabeprazole sodium obtained is 99.4% by HPLC.

Example 7

Preparation of Amorphous Rabeprazole Sodium by the Solvent System Comprising Methylethylketone, Acetone, and Toluene 10.0 grams of rabeprazole sodium compound is dissolved in a solution prepared by mixing 50 ml of methylethylketone, 5 ml of acetone and 150 ml of toluene. The solution is heated to 45° C. until the solution is clear. The insoluble impurities are removed by filtration. The resultant clear solution is gradually cooled to room temperature (about 25° C.) and, in the meantime, is stirred slowly and continuously for at least 12 hours to obtain the solution containing the separated solid of rabeprazole sodium. The separated rabeprazole sodium is then filtered out and washed by the solvent mixture of acetone and toluene. After dried, the X-ray diffraction pattern of this final product does not have any distinct diffraction peaks so that the final product of this process is amorphous. The final product of amorphous rabeprazole sodium obtained is 8.9 grams, so the yield of this process is 89%. The purity of this amorphous rabeprazole sodium obtained is 99.5% by HPLC.

Example 8

Preparation of Amorphous Rabeprazole Sodium by the Solvent System Comprising Methylethylketone and Ether 10.0 grams of rabeprazole sodium compound is dissolved in a solution prepared by mixing 50 ml of methylethylketone and 20 ml of ether. The solution is heated to 40° C. until the solution is clear. The insoluble impurities are removed by filtration. The resultant clear solution is gradually cooled to room temperature (about 25° C.) and, in the meantime, is stirred slowly and continuously for at least 3 hours to obtain the solution containing the separated solid of rabeprazole sodium. The separated rabeprazole sodium is then filtered out and washed by the solvent mixture of methylethylketone and ether. After dried, the X-ray diffraction pattern of this final product does not have any distinct diffraction peaks so that the final product of this process is amorphous. The final product of amorphous rabeprazole sodium obtained is 7.9 grams, so the yield of this process is 79%. The purity of this amorphous rabeprazole sodium obtained is 99.2% by HPLC.

Although the particular embodiments of the invention have been described in detail for purpose of illustration, it will be understood by one of ordinary skill in the art that numerous variations will be possible to the disclosed embodiments without going outside the scope of the invention as disclosed in the claims.

What is claimed is:

1. A process for preparing rabeprazole sodium comprising the steps of:
   (a) contacting rabeprazole sodium compound with a solvent system to thereby obtain a clear solution under a first temperature ranging from 25 to 50, wherein said solvent system is a mixture comprising a ketone solvent and a cyclic hydrocarbon solvent, a mixture comprising a ketone solvent and an ether solvent, or a mixture comprising a heterocyclic organic solvent and a cyclic hydrocarbon solvent, and wherein:
      when said solvent system is the mixture comprising the ketone solvent and the cyclic hydrocarbon solvent, and the cyclic hydrocarbon solvent is present in a vol/vol ratio of the cyclic hydrocarbon solvent to the ketone solvent of 0.3 to 5;
      when said solvent system is the mixture comprising the ketone solvent and the ether solvent, and the ketone solvent is present in a vol/vol ratio of the ketone solvent to the ether solvent of 1.5 to 5; and
      when said solvent system is the mixture comprising the heterocyclic organic solvent and the cyclic hydrocarbon solvent, and the cyclic hydrocarbon solvent is present in a vol/vol ratio of the cyclic hydrocarbon solvent to the heterocyclic organic solvent of 0.2 to 5;
   (b) stirring said clear solution of step (a) under a second temperature for more than 3 hours to obtain a solution containing resultant separated solid, wherein said second temperature ranges from 25 to 50;
   (c) filtering said solution containing resultant separated solid obtained from step (b) to obtain a wet solid; and
   (d) drying said wet solid to obtain an amorphous rabeprazole sodium compound.

2. The process of claim 1, wherein when said solvent system is the mixture comprising the ketone solvent and the cyclic hydrocarbon solvent, the ketone solvent is selected from the group consisting of methylethylketone, acetone, and mixtures thereof and the cyclic hydrocarbon solvent is cyclohexane, cycloheptane, benzene, toluene, or xylene.

3. The process of claim 1, wherein when said solvent system is the mixture comprising the ketone solvent and the ether solvent, the ketone solvent is selected from the group consisting of methylethylketone, acetone, and mixtures thereof and the ether solvent is diethyl ether, isopropylethyl ether, or diisopropyl ether.

4. The process of claim 1, wherein when said solvent system is the mixture comprising the heterocyclic organic solvent and the cyclic hydrocarbon solvent, the heterocyclic organic solvent is tetrahydrofuran and the cyclic hydrocarbon solvent is cyclohexane, cycloheptane, benzene, toluene, or xylene.

5. The process of claim 1, wherein said cyclic hydrocarbon solvent is present in a vol/vol ratio of the cyclic hydrocarbon solvent to the ketone solvent of 0.5 when the cyclic hydrocarbon solvent is cyclohexane, or 3 when the cyclic hydrocarbon solvent is toluene.

6. The process of claim 1, wherein when said solvent system is the mixture comprising the heterocyclic organic solvent and the cyclic hydrocarbon solvent, said cyclic hydrocarbon solvent is present in a vol/vol ratio of the cyclic hydrocarbon solvent to the heterocyclic organic solvent of 5 when the cyclic hydrocarbon solvent is toluene, 0.6 when the cyclic hydrocarbon solvent is cyclohexane, or 2.4 when the cyclic hydrocarbon solvent is xylene.

7. The process of claim 1, wherein said solvent system comprises an acetone, a methyethylketone solvent and a cyclic hydrocarbon solvent with a volume ratio of 1:6-10:20-30.

8. The process of claim 1, wherein the step (b) further comprises a step of cooling said solution of step (a) gradually to at least 10.

9. The process of claim 1, wherein the step (c) further comprises a step of washing said wet solid with said solvent system.

10. The process of claim 1, wherein the yield of said amorphous rabeprazole sodium is more than 79% and said amorphous rabeprazole sodium obtained has a purity of more than 99% by HPLC.

11. The process of claim 1, wherein said rabeprazole sodium compound before contacting with said solvent system of step (a) is an extract crude obtained from condensing a solution comprising rabeprazole compound and sodium hydroxide.

* * * * *